(12) United States Patent
Kawai et al.

(10) Patent No.: US 12,038,060 B2
(45) Date of Patent: Jul. 16, 2024

(54) FLEXIBLE MEMBER

(71) Applicant: NHK SPRING CO., LTD., Kanagawa (JP)

(72) Inventors: Yosuke Kawai, Kanagawa (JP); Shimpei Kurokawa, Kanagawa (JP); Yuki Hayakawa, Kanagawa (JP)

(73) Assignee: NHK SPRING CO., LTD., Kanagawa (JP)

( * ) Notice: Subject to any disclaimer, the term of this patent is extended or adjusted under 35 U.S.C. 154(b) by 280 days.

(21) Appl. No.: 17/601,927

(22) PCT Filed: Apr. 13, 2020

(86) PCT No.: PCT/JP2020/016306
§ 371 (c)(1),
(2) Date: Oct. 7, 2021

(87) PCT Pub. No.: WO2020/209388
PCT Pub. Date: Oct. 15, 2020

(65) Prior Publication Data
US 2022/0145956 A1      May 12, 2022

(30) Foreign Application Priority Data
Apr. 11, 2019   (JP) .................. 2019-075950

(51) Int. Cl.
*F16F 3/02*       (2006.01)
*B25J 18/06*      (2006.01)
*A61B 34/30*      (2016.01)

(52) U.S. Cl.
CPC .............. *F16F 3/02* (2013.01); *B25J 18/06* (2013.01); *A61B 34/30* (2016.02); *F16F 2226/048* (2013.01)

(58) Field of Classification Search
CPC ........ F16F 3/02; F16F 2226/048; B25J 18/06; B25J 9/0015
See application file for complete search history.

(56) References Cited

U.S. PATENT DOCUMENTS 5,072,917 A     12/1991   Pleva
6,068,250 A  *   5/2000   Hawkins ................. F16F 1/328
                                                          267/164

(Continued)

FOREIGN PATENT DOCUMENTS

DE            8901778         5/1989
DE     202011002271 U1  *     6/2011  ......... B23K 15/0006

(Continued)

OTHER PUBLICATIONS

"Search Report of Europe Counterpart Application", dated May 16, 2022, p. 1-p. 7.

(Continued)

*Primary Examiner* — Melody M Burch
(74) *Attorney, Agent, or Firm* — JCIPRNET

(57) ABSTRACT

The present invention provides a flexible member having excellent load resistance and flexibility while achieving a reduction in size. This flexible member is provided with: a main body part which includes multiple wave washers that are stacked in an axial direction and are joined to one another by multiple joint parts, and which is capable of bending relative to the axial direction by elastic deformation of the wave washers; and easily deformable parts formed between the joint parts that are adjacent to one another in the circumferential direction in each wave washer.

5 Claims, 16 Drawing Sheets

(56) References Cited

U.S. PATENT DOCUMENTS

| | | | | |
|---|---|---|---|---|
| 6,758,465 B1 * | 7/2004 | Greenhill | ............... | F16F 1/06 |
| | | | | 267/162 |
| 2003/0222385 A1 | 12/2003 | Cai et al. | | |
| 2016/0235274 A1 | 8/2016 | Graham | | |

FOREIGN PATENT DOCUMENTS

| | | | | | |
|---|---|---|---|---|---|
| GB | 2389161 A | * | 12/2003 | ............. | F16F 1/328 |
| JP | S50-058154 | | 5/1975 | | |
| JP | 3789299 B2 | * | 6/2006 | | |
| JP | 2014038075 | | 2/2014 | | |
| JP | 2016075390 | | 5/2016 | | |
| RU | 187293 U1 | * | 2/2019 | | |
| WO | WO-2006128676 A1 | * | 12/2006 | ........... | F01N 13/102 |
| WO | 2015066536 | | 5/2015 | | |

OTHER PUBLICATIONS

"Office Action of China Counterpart Application", dated Jun. 1, 2023, with English translation thereof, p. 1-p. 13.
"International Search Report (Form PCT/ISA/210) of PCT/JP2020/016306", dated Jul. 7, 2020, with English translation thereof, pp. 1-4.
"Search Report of Europe Counterpart Application", dated Oct. 25, 2023, pp. 1-4.
"Office Action of Europe Counterpart Application", dated Oct. 25, 2023, pp. 1-4.
"Office Action of China Counterpart Application", dated Nov. 1, 2023, with English translation thereof, p. 1-p. 10.
"Office Action of China Counterpart Application", issued on Feb. 22, 2024, with English translation thereof, p. 1-p. 11.

* cited by examiner (A)

(B)

(A)

(B)

(A)

(B)

(A)

(B)

(A)

(B)

(A)

(B)

US 12,038,060 B2

FLEXIBLE MEMBER

CROSS-REFERENCE TO RELATED APPLICATION

This application is a 371 application of the international PCT application serial no. PCT/JP2020/016306, filed on Apr. 13, 2019, which claims the priority benefit of Japan application no. 2019-075950, filed on Apr. 11, 2019. The entirety of each of the above-mentioned patent applications is hereby incorporated by reference herein and made a part of this specification.

TECHNICAL FIELD

The present invention relates to a flexible member provided for a joint functioning part of a robot or the like.

BACKGROUND ART

Some robots, manipulators, actuators, and the like in various fields have a joint functioning part capable of performing bending operation using a flexible member. Regarding a flexible member used in such a joint functioning part, Japanese Patent Laid-Open No. 2014-38075 discloses a coil spring.

A coil spring can secure a high degree of freedom with respect to bending operation of a joint functioning part. However, there has been a limit to reduction in size of a coil spring due to the need to secure load resistance and flexibility.

SUMMARY OF INVENTION

Technical Problem

A problem to be solved is that there is a limit in securing load resistance and flexibility while achieving reduction in size.

Solution to Problem

The present invention provides a flexible member which can have excellent load resistance and flexibility while achieving reduction in size. This flexible member includes a main body part that has a plurality of wave washers stacked in an axial direction and joined to each other by a plurality of joint parts and is able to be bent with respect to the axial direction due to elastic deformation of the wave washers, and easily deformable parts that are formed between the joint parts adjacent to each other in a circumferential direction in each of the wave washers and are more readily deformable than other portions in the wave washers.

Advantageous Effects of Invention

According to the present invention, the main body part of the flexible member can be bent due to deformation of the plurality of wave washers. Therefore, it is possible to obtain a flexible member having excellent load resistance and flexibility while achieving reduction in size.

Furthermore, in the present invention, since the easily deformable parts are deformed between the joint parts in each of the wave washers when the main body part is bent, deformation in the vicinity of the joint parts in the wave washers can be reduced and a stress can be alleviated. As a result, the present invention can improve durability of a flexible member.

DESCRIPTION OF EMBODIMENT

An objective of obtaining a flexible member which can have excellent load resistance and flexibility while achieving reduction in size is realized while durability is improved.

That is, a flexible member includes a main body part in which a plurality of wave washers is stacked in an axial direction and joined to each other by a plurality of joint parts and which is able to be bent with respect to the axial direction due to elastic deformation of the wave washers, and easily deformable parts which are formed between the joint parts adjacent to each other in a circumferential direction in each of the wave washers and are more readily deformable than other portions in the wave washers.

In the constitution, the easily deformable parts may include: portions of the wave washer having a relatively small dimension in a radial direction, or portions of the wave washer having a relatively small plate thickness.

The plurality of joint parts may include: welded parts in linear shape, being extended from an inner circumferential side toward an outer circumferential side in each of the wave washers.

In this case, in the constitution, each of the joint parts may include a pair of welded parts, and the pair of welded parts may gradually separate from each other in the circumferential direction from the inner circumferential side toward the outer circumferential side in the wave washer.

The pair of welded parts may have a V-shape in which the welded parts overlap each other on the inner circumferential side in the wave washer.

In this case, an opening angle between the pair of welded parts may be 20 degrees.

In the constitution, each of the plurality of wave washers may include a plurality of mountain parts and valley parts between the mountain parts in the circumferential direction, mountain parts and valley parts of adjacent wave washers may abut each other, and abutment portions of the mountain parts and the valley parts may be joined to each other by the joint parts.

Example 1

[Manipulator]

Figure 1:
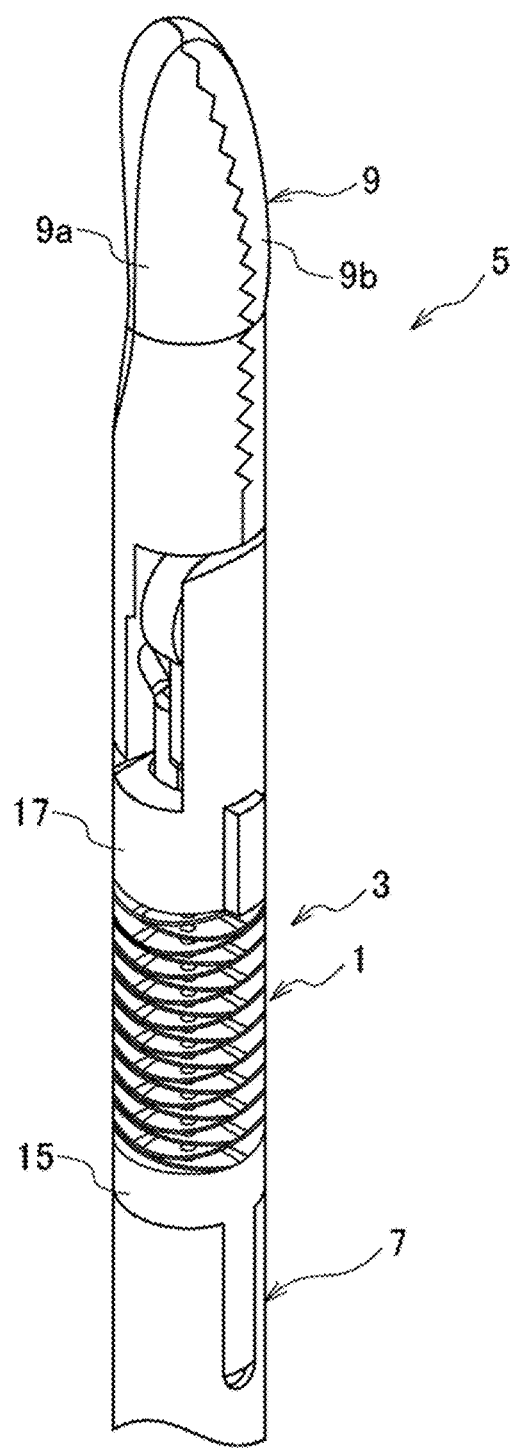
FIG. 1 is a perspective view illustrating a manipulator using a flexible member according to an Example 1 of the present invention.
Figure 2:
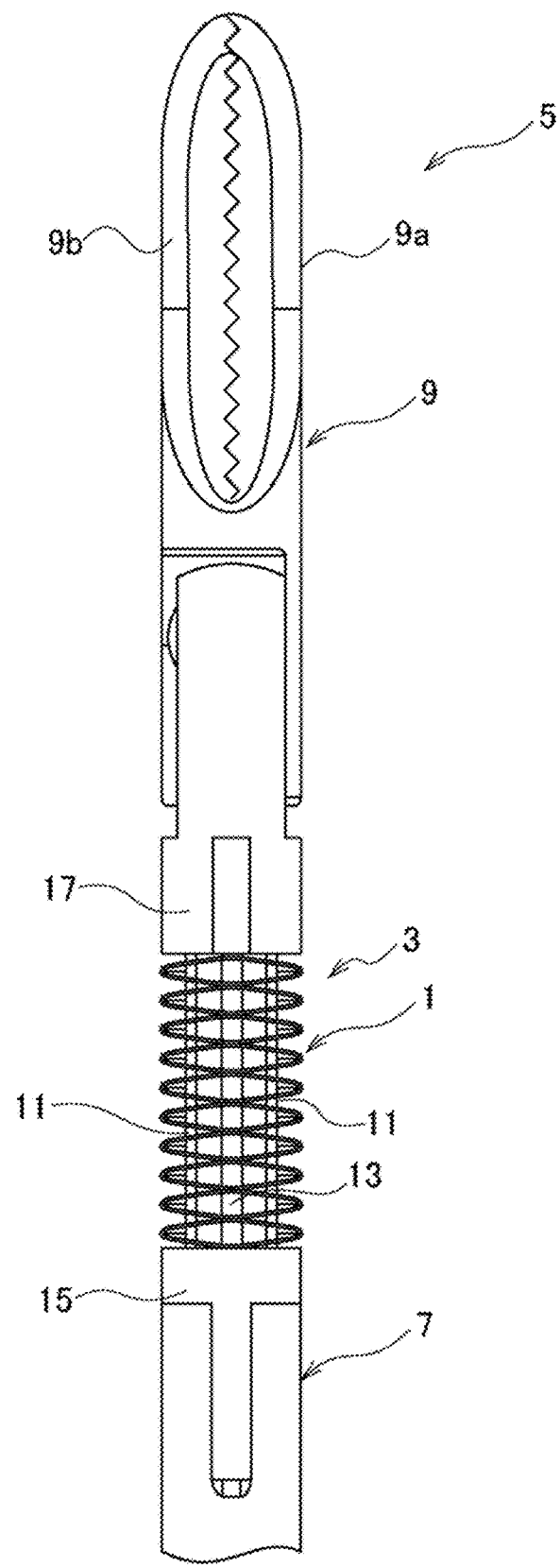
FIG. 2 is a front view illustrating the manipulator in FIG. 1.
Figure 3:
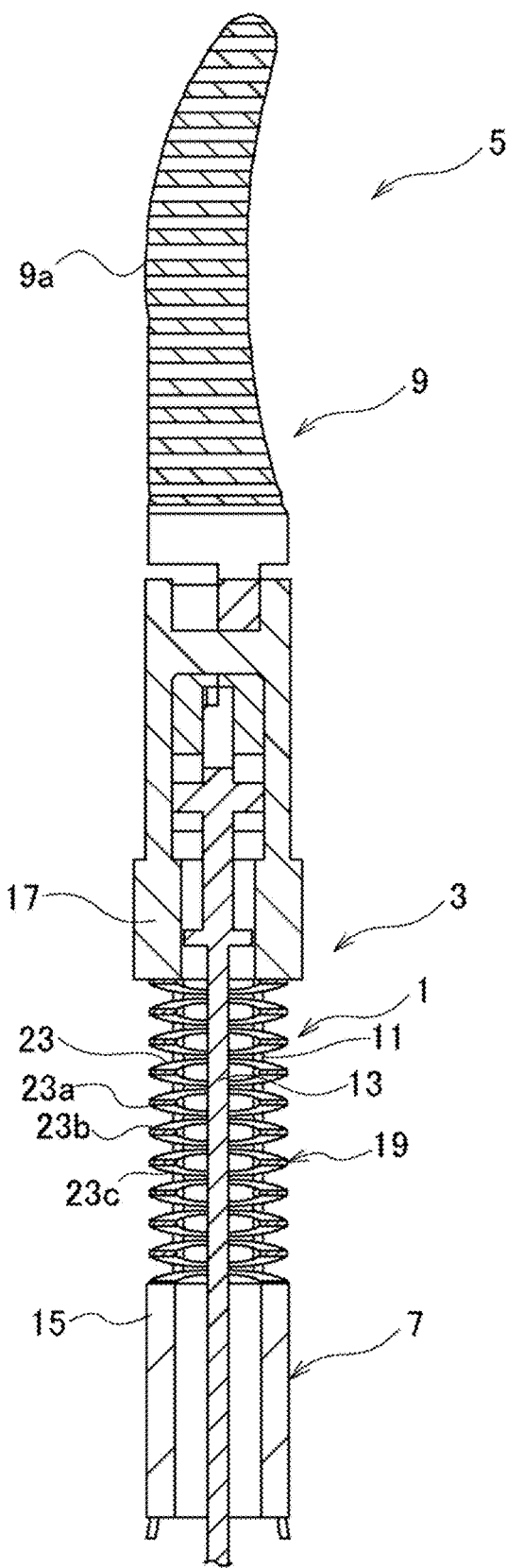
FIG. 3 is a cross-sectional view of the manipulator in FIG. 1.

FIG. 1 is a perspective view illustrating a manipulator using a flexible member according to an Example 1 of the present invention, FIG. 2 is a front view of the same, and FIG. 3 is a cross-sectional view of the same.

The present example will be described regarding a medical manipulator 5 as an example of a robot, a manipulator, or an actuator which has a joint functioning part 3 using a flexible member 1.

The manipulator 5 constitutes a tip of a robot arm of a surgical robot and is operated by a doctor or the like. The manipulator 5 may be a manual manipulator which is directly operated by a doctor or the like without being attached to a surgical robot. In addition, a robot, a manipulator, or an actuator in which the flexible member 1 can be applied is not limited to the manipulator 5, and the flexible member 1 may be adopted in other fields such as industrial robots.

The manipulator 5 includes a shaft part 7, the joint functioning part 3, and an end effector 9.

The shaft part 7 is formed to have a hollow tubular shape, for example, a cylindrical shape. Driving wires 11 for driving the joint functioning part 3 or a push-pull cable 13 for driving the end effector 9 passes through the inside of the shaft part 7. The end effector 9 is provided at a tip of the shaft part 7 with the joint functioning part 3 therebetween.

The joint functioning part 3 performs bending operation with respect to an axial direction in response to an operation of the driving wires 11. The axial direction denotes a direction along an axial center of the flexible member 1, which will be described below. However, there is no need for the axial direction to be a direction strictly parallel to the axial center. Therefore, the axial direction also includes a direction slightly inclined with respect to the axial center. Details of the joint functioning part 3 will be described below.

The end effector 9 is an instrument which is attached to a movable part 17 of the joint functioning part 3 and performs operation according to a purpose. The end effector 9 of the present example is a forceps and includes a pair of clasping parts 9a and 9b. This end effector 9 can be directed in a desired direction in response to bending operation of the joint functioning part 3. In addition, the pair of clasping parts 9a and 9b can be opened and closed in response to an operation of the push-pull cable 13.

The end effector 9 is not limited to a forceps, for example, it can be scissors, a clasping retractor, a needle driver, a camera, or the like.

[Joint Functioning Part]

Figure 4:
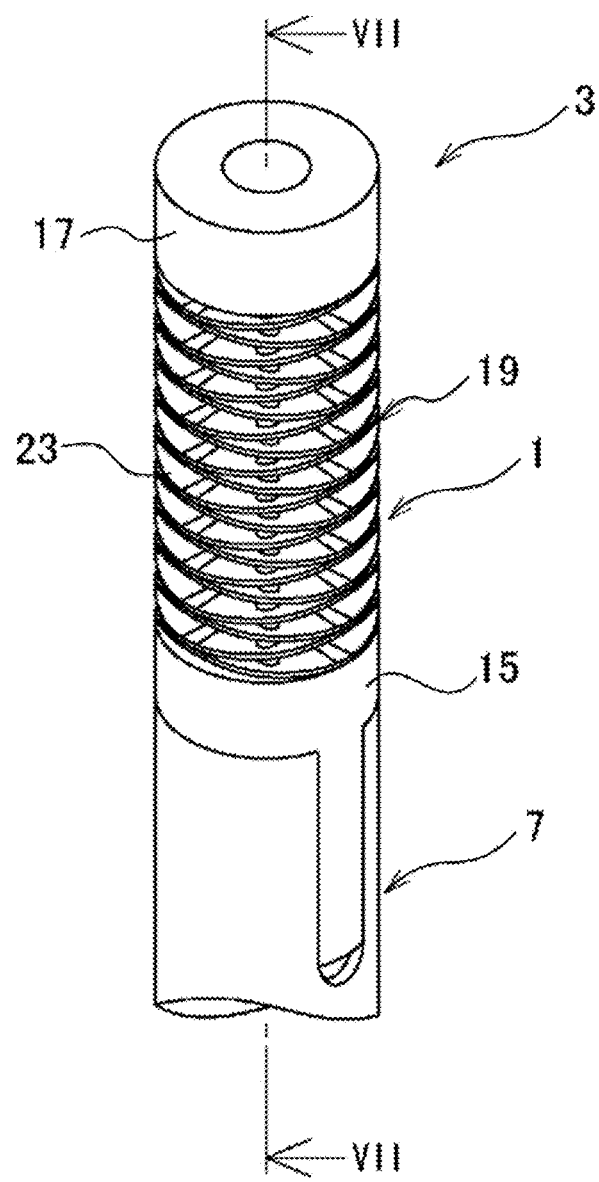
FIG. 4 is a perspective view mainly illustrating a joint functioning part in which a part of the manipulator in FIG. 1 is omitted.
Figure 5:
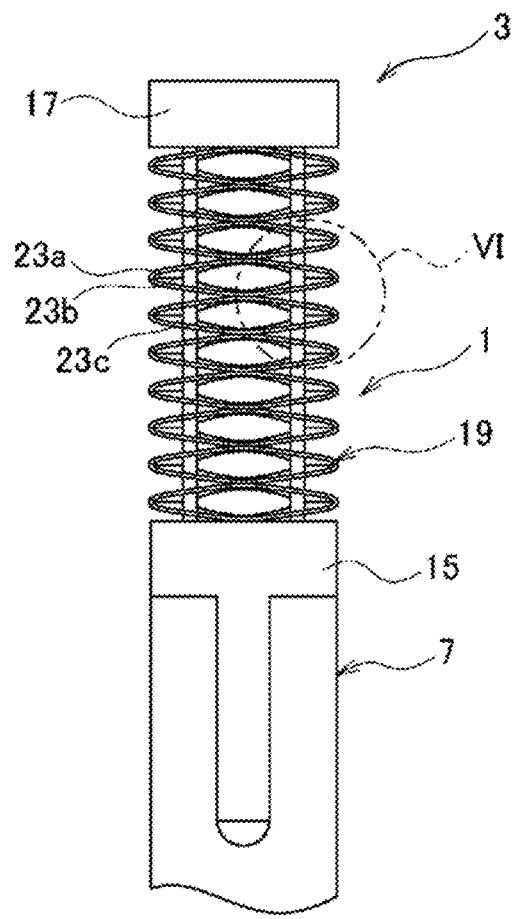
FIG. 5 is a side view mainly illustrating the joint functioning part in FIG. 4.
Figure 6:
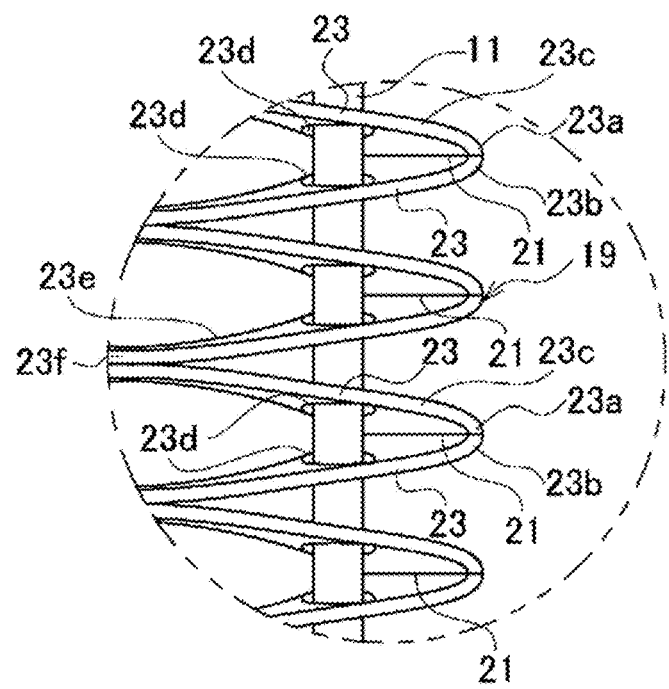
FIG. 6 is an enlarged view of the VI part in FIG. 5.
Figure 7:
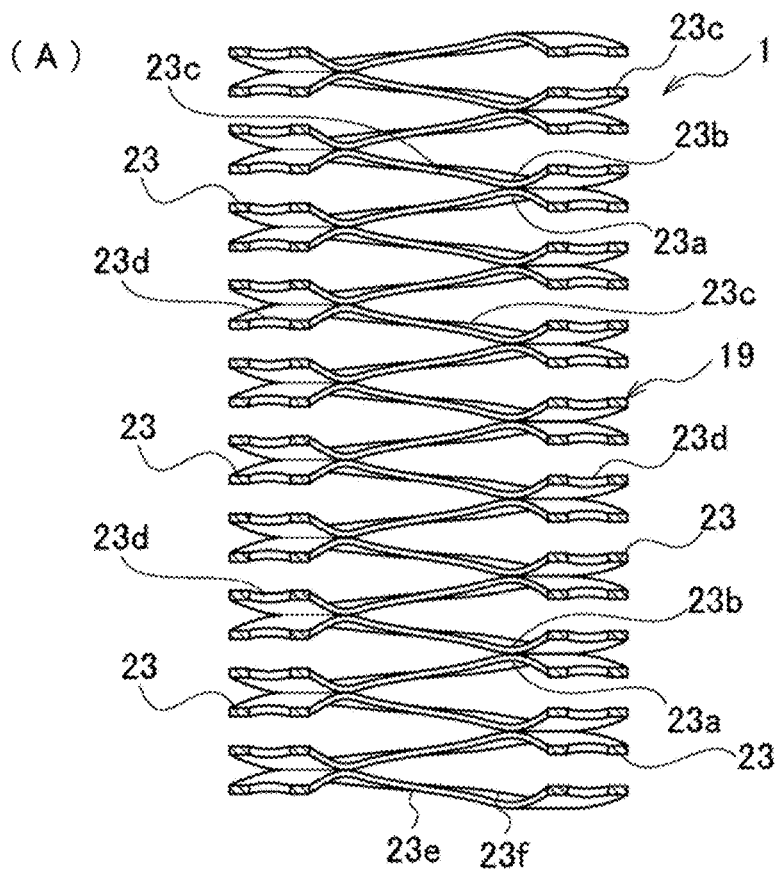
In FIG. 7, (A) and (B) are cross-sectional views illustrating a flexible member of the joint functioning part along line VII-VII in FIG. 4, in which (A) of FIG. 7 illustrates the flexible member at a normal time, and (B) of FIG. 7 illustrates the flexible member at the time of being bent.
Figure 7:
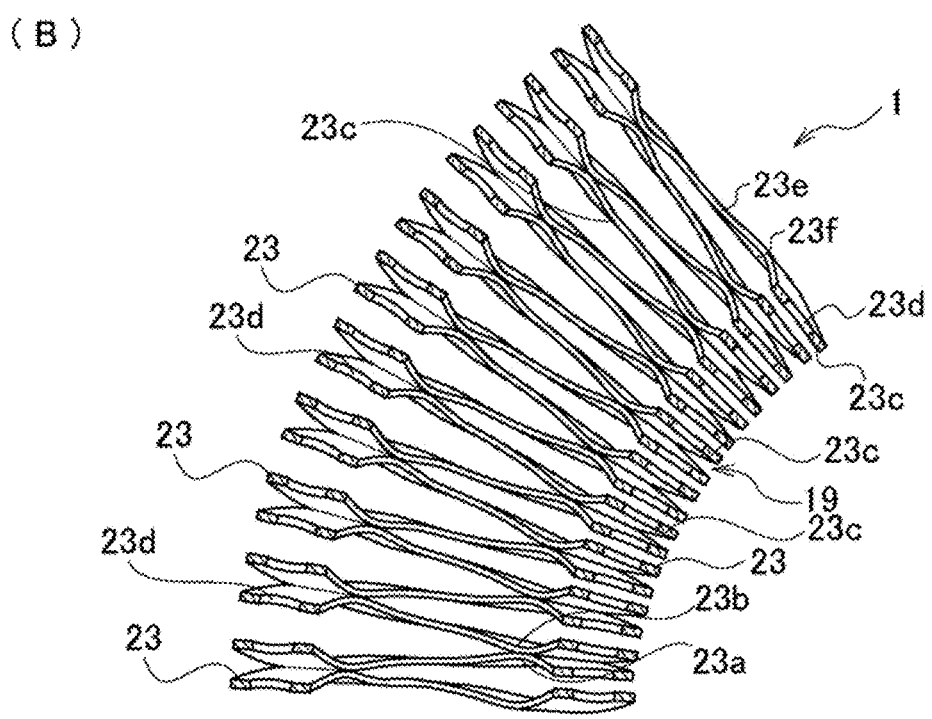

FIG. 4 is a perspective view mainly illustrating the joint functioning part 3 in which a part of the manipulator 5 in FIG. 1 is omitted, FIG. 5 is a side view of the same, and FIG. 6 is an enlarged view of the VI part in FIG. 5. In FIG. 7, (A) and (B) are cross-sectional views illustrating the flexible member 1 of the joint functioning part 3 along line VII-VII in FIG. 4, in which (A) of FIG. 7 illustrates the flexible member 1 at a normal time, and (B) of FIG. 7 illustrates the flexible member 1 at the time of being bent.

As in FIG. 1 to (B) of FIG. 7, the joint functioning part 3 includes a base part 15, the movable part 17, and the flexible member 1.

The base part 15 is formed of a metal or the like to have a columnar shape and is attached to the tip of the shaft part 7. The push-pull cable 13 is inserted through an axial center part of the base part 15 in the axial direction. Around the push-pull cable 13, the driving wires 11 are inserted through the base part 15 in the axial direction.

The movable part 17 is formed of a metal or the like to have a columnar shape and is attached to the end effector 9. An axial center part of the movable part 17 is inserted through the push-pull cable 13. A tip of the push-pull cable 13 is linked to the end effector 9.

This movable part 17 is supported by the base part 15 with the flexible member 1 therebetween. Tip parts of the driving wires 11 are fixed to the movable part 17. For this reason, the movable part 17 is deformed with respect to the base part 15 due to an operation of the driving wires 11 and can direct the end effector 9 in a desired direction.

The flexible member 1 enables the joint functioning part 3 to perform bending operation. The flexible member 1 is interposed between the base part 15 and the movable part 17. The flexible member 1 is bent in response to deformation of the movable part 17 with respect to the base part 15. The driving wires 11 and the push-pull cable 13 pass through the flexible member 1 in the axial direction.

In the flexible member 1, both end parts of a main body part 19 are fixed to the base part 15 and the movable part 17, respectively. This fixing can be performed using joint parts 21 which will be described below or a different fixing devices.

The main body part 19 has a plurality of wave washers 23. The wave washers 23 are stacked in the axial direction, and wave washers 23 adjacent to each other in the axial direction are joined to each other. The main body part 19 can be bent due to elastic deformation of the wave washers 23.

[Wave Washer]

Figure 8:
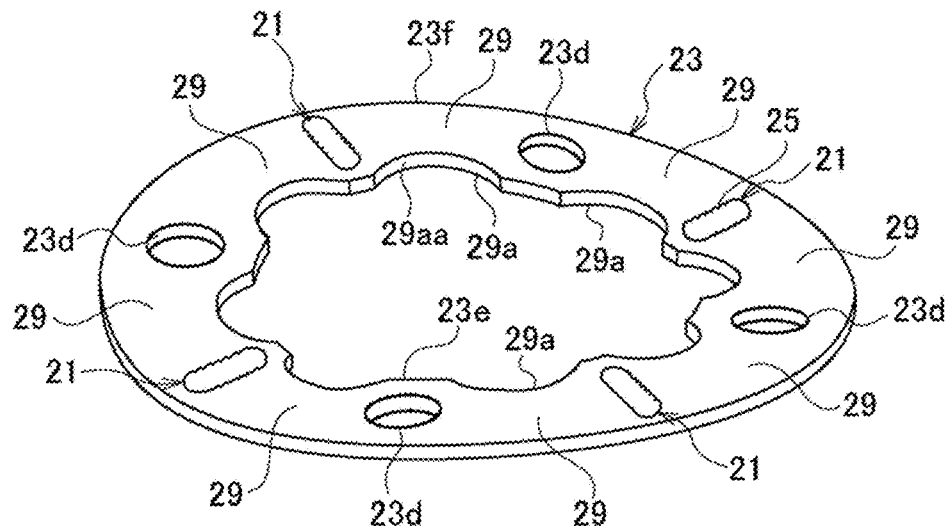
FIG. 8 is a perspective view illustrating a wave washer.
Figure 9:
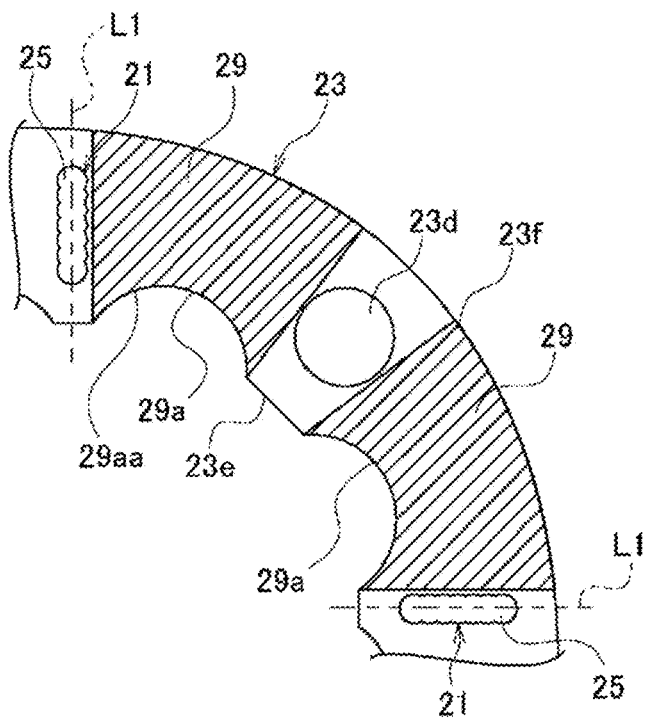
FIG. 9 is an enlarged plan view illustrating a main part in FIG. 8.
Figure 10:
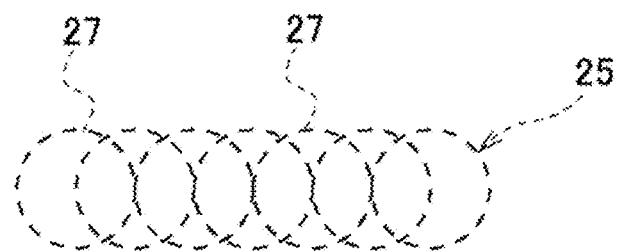
FIG. 10 is a plan view conceptually illustrating welding spots of a welded part of a joint part.

FIG. 8 is a perspective view illustrating the wave washers 23. FIG. 9 is an enlarged plan view illustrating a main part in FIG. 8. FIG. 10 is a plan view conceptually illustrating welding spots 27 of a welded part 25 of the joint part 21.

As in FIG. 4 to FIG. 8, each of the wave washers 23 is a plate member formed of a metal or the like to have a closed ring shape. The wave washers 23 of the present example are plate members formed of stainless steels to have toric shapes. A width of the wave washer 23 between inner and outer circumferences 23e and 23f in a radial direction and a plate thickness thereof are uniform in a circumferential direction. However, the widths and the plate thicknesses of the wave washers 23 may not be uniform in the circumferential direction.

Each of the wave washers 23 has a plurality of mountain parts 23a and valley parts 23b in the circumferential direction. Each of the valley parts 23b is provided between mountain parts 23a adjacent to each other in the circumferential direction. Each of the wave washers 23 of the present example has two mountain parts 23a facing each other in the radial direction and has two valley parts 23b facing each other in the radial direction between the mountain parts 23a. Therefore, in the present example, the mountain parts 23a and the valley parts 23b are alternately provided at intervals of 90 degrees in the circumferential direction.

The mountain parts 23a and the valley parts 23b lie from the inner circumference 23e to the outer circumference 23f of the wave washer 23 in the radial direction. The mountain parts 23a and the valley parts 23b are formed to be curved in arc shapes in a direction opposite to the axial direction. In wave washers 23 adjacent to each other in the axial direction, the mountain parts 23a of the wave washer 23 on one side abut the valley parts 23b of the wave washer on the other side. Due to expansion and contraction of the mountain parts 23a and the valley parts 23b, each of the wave washers 23 can be deformed due to elastic expansion and contraction in the axial direction.

Regarding the mountain parts 23a and the valley parts 23b abutting each other, abutment portions of both the parts are joined to each other by the joint parts 21. Accordingly, the stacked state of the main body part 19 of the flexible member 1 is retained.

The joint parts 21 include: welded parts 25 in linear shape, being extended from the inner circumference 23e side to the outer circumference 23f side of the wave washer 23. The welded parts 25 of the present example are formed to have continuously linear shapes on first lines L1 extending in a radiating direction from the center of the wave washer 23. The end parts of the joint parts 21 on the inner circumferential side and the outer circumferential side are disposed at intervals in the radial direction from the inner circumference 23e and the outer circumference 23f of the wave washer 23, respectively.

The welded parts 25 are formed by spot welding. The welded parts 25 are disposed such that the centers of the welding spots 27 are positioned on the first line L1. Adjacent welding spots 27 overlap each other or come into contact with each other in a plan view, and thus the welded parts 25 have continuously linear shapes. In the present example, adjacent welding spots 27 overlap each other.

The welded parts 25 can be suitably set in accordance with a difference between deformation amounts in the inner and outer circumferences 23e and 23f of the wave washer 23. For example, the welded parts 25 may be provided in dashed line shapes by separating adjacent welding spots 27 from each other.

In each of the wave washers 23, the mountain parts 23a and the valley parts 23b are connected to each other through inclined parts 23c. The inclined parts 23c are inclined in the circumferential direction and have slightly twisted shapes between the inner circumference 23e and the outer circumference 23f.

Insertion holes 23d serving as through parts through which the driving wires 11 pass are provided in the inclined parts 23c. As a result, a plurality of insertion holes 23d is provided in the circumferential direction of the main body part 19. In the present example, four driving wires 11 are individually provided at intervals of 90 degrees in the circumferential direction. Therefore, in accordance with this, four insertion holes 23d are individually provided at intervals of 90 degrees in the circumferential direction in each of the wave washers 23.

The insertion holes 23d communicate with each other in the axial direction between the inclined parts 23c of wave washers 23 adjacent to each other in the axial direction. The driving wires 11 are inserted through the insertion holes 23d communicating with each other. Due to this insertion, the flexible member 1 functions as a through part through which the driving wires 11 pass in the axial direction and as a guide retaining the driving wires 11 at a predetermined position.

The insertion holes 23d have substantially circular shapes and have diameters larger than the diameters of the driving wires 11. The difference between the diameters allows inclination and deformation of the inclined parts 23c. The shapes of the insertion holes 23d are not limited to circular shapes and may have different shapes such as rectangular shapes.

The shapes, the materials, and the like of the wave washers 23 can be suitably changed in accordance with characteristics or the like required for the flexible member 1. The number and the radii of curvature of the mountain parts 23a and the valley parts 23b, the inclination angles of the inclined parts 23c, and the like can also be suitably changed in accordance with characteristics or the like required for the flexible member 1.

The wave washer 23 of the present example has easily deformable parts 29. In FIG. 9, in order to facilitate the understanding, the easily deformable parts 29 are illustrated by double oblique lines.

The easily deformable parts 29 are individually formed between the joint parts 21 adjacent to each other in the circumferential direction in each of the wave washers 23. The easily deformable parts 29 have an easily deformable constitution compared to other portions in the wave washer 23 when the main body part 19 of the flexible member 1 is bent.

Therefore, in each of the wave washers 23, since the easily deformable parts 29 are individually deformed between the joint parts 21 when the main body part 19 of the flexible member 1 is bent, deformation in the vicinity of the joint parts 21 can be reduced and a stress can be alleviated.

The easily deformable parts 29 of the present example include: portions of the wave washer 23 having a relatively small dimension in the radial direction. Specifically, in the easily deformable parts 29, the dimension of the wave washer 23 in the radial direction is set to be relatively small due to recessed parts 29a in the radial direction formed in the inner circumference 23e of the wave washer 23. In the easily deformable parts 29, a cross-sectional second moment of the wave washer 23 is partially reduced so that the easily deformable parts 29 are more readily deformable than other portions.

The easily deformable parts 29 are disposed on both sides of the insertion holes 23d in the circumferential direction. When the insertion holes 23d are not provided, a single continuous easily deformable part may be formed between the joint parts 21 adjacent to each other in the circumferential direction.

The recessed parts 29a correspond to the easily deformable parts 29 on both sides of the insertion holes 23d, and a pair of recessed parts 29a is provided with respect to each of the joint parts 21. Each of the recessed parts 29a is formed to have a cutout shape from the inner circumference 23e toward the outer circumference 23f of the wave washer 23.

Inner surfaces 29aa of the recessed parts 29a have arc shapes. However, regarding the shapes of the inner surfaces 29aa, different shapes can be employed as long as the cross-sectional second moment of the easily deformable parts 29 can be reduced.

[Bending Operation of Joint Functioning Part]

In the joint functioning part 3, when a doctor operates the manipulator 5, the flexible member 1 is bent by pulling any one of the driving wires 11. This joint functioning part 3 can be bent in all directions through 360 degrees by pulling some driving wires 11 in combination.

When bending is performed by pulling at least any one of the driving wires 11, in the flexible member 1, as in (B) of FIG. 7, the mountain parts 23a and the valley parts 23b are compressed at bending inner side portions with respect to a neutral axis and the mountain parts 23a and the valley parts 23b are extended at bending outer side portions with respect to the neutral axis.

Due to such deformation, the inclined parts 23c through which the operated driving wires 11 are inserted approach each other, and the flexible member 1 in its entirety is bent. Accordingly, the present example realizes bending operation having highly linear load characteristics of a bending angle and a load.

In deformation of the wave washers 23 at the time of being bent, the easily deformable parts 29 can be actively deformed between the joint parts 21 adjacent to each other in the circumferential direction. For this reason, the deformation amounts in the vicinity of the joint parts 21 are reduced, and a stress acting on portions in the vicinity of the joint parts 21 is reduced.

[Stress Distribution]

Figure 11:
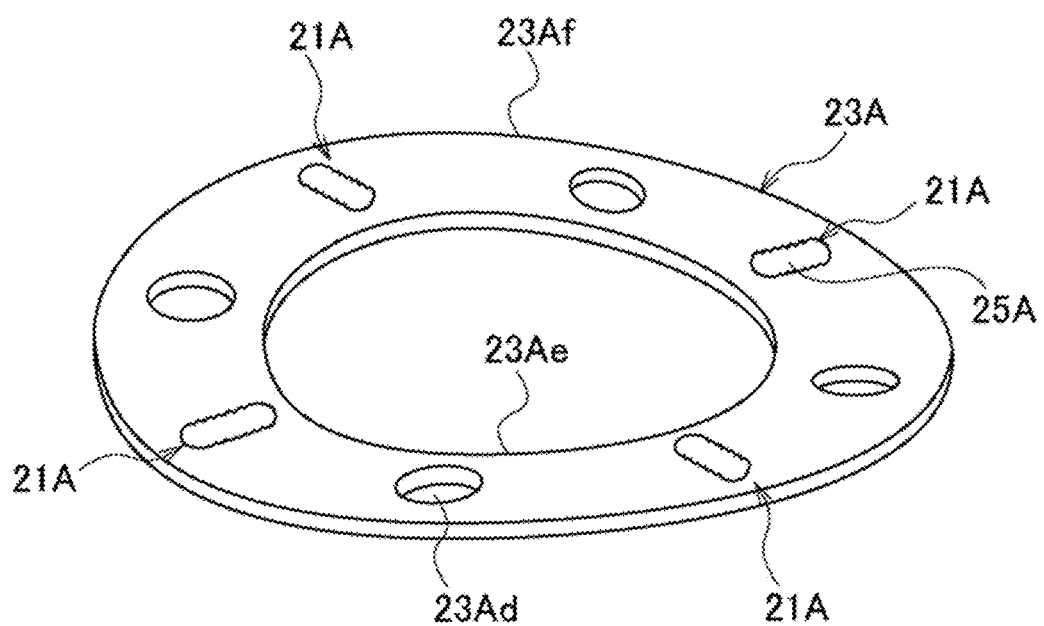
FIG. 11 is a perspective view illustrating a wave washer according to a comparative example.
Figure 12:
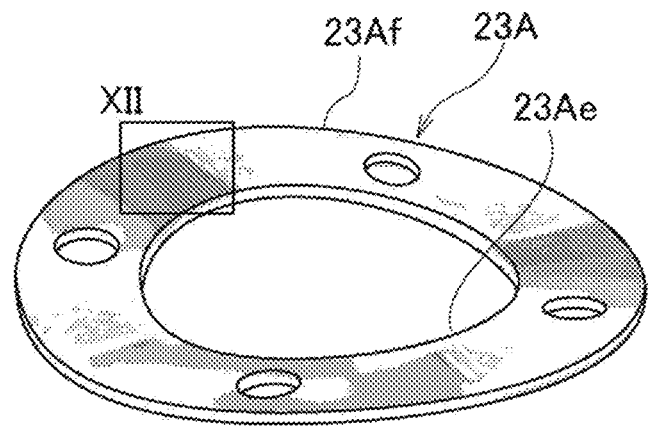
In FIG. 12, (A) and (B) illustrate a stress distribution of the wave washer according to the comparative example in FIG. 11, in which (A) of FIG. 12 illustrates a perspective view of the wave washer in its entirety, and (B) of FIG. 12 is an enlarged view of the XII part in (A) of FIG. 12.
Figure 12:
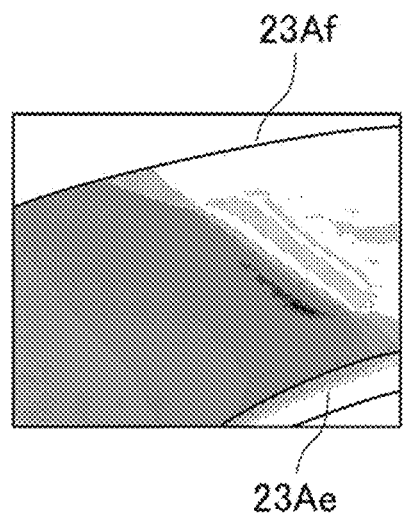
Figure 13:
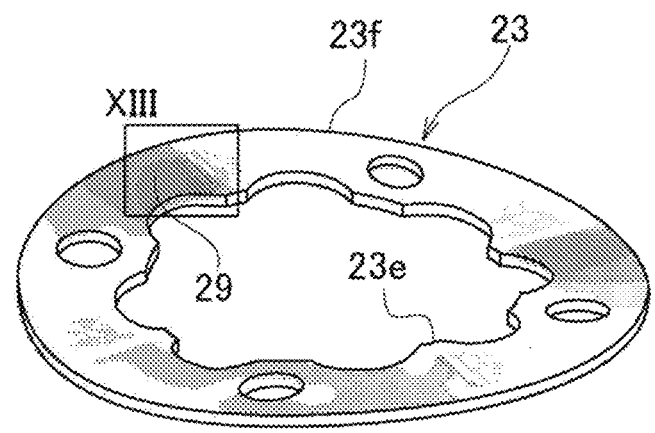
In FIG. 13, (A) and (B) illustrate a stress distribution of the wave washer in FIG. 8, in which (A) of FIG. 13 illustrates a perspective view of the wave washer in its entirety, and (B) of FIG. 13 is an enlarged view of the XIII part in (A) of FIG. 13.
Figure 13:
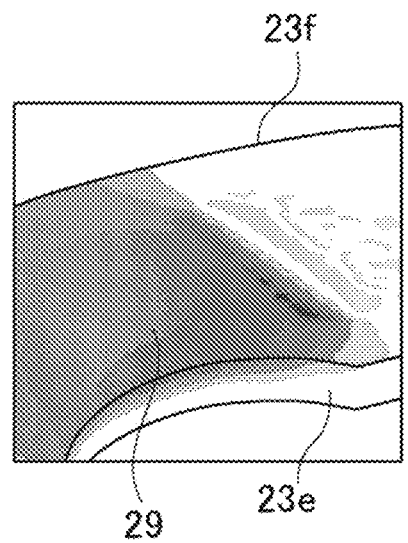

FIG. 11 is a perspective view illustrating a wave washer 23A having joint parts 21A according to a comparative example. In FIG. 12, (A) and (B) illustrate a stress distribution of the wave washer 23A according to the comparative example, in which (A) of FIG. 12 is a perspective view of the wave washer 23A in its entirety, and (B) of FIG. 12 is an enlarged view of the XII part in (A) of FIG. 12. In FIG. 13, (A) and (B) illustrate a stress distribution of the wave washer 23 according to the Example 1, in which (A) of FIG. 13 is a perspective view of the wave washer 23 in its entirety, and (B) of FIG. 13 is an enlarged view of the XIII part in (A) of FIG. 13.

Stress distributions of the wave washers 23A used in a flexible member (not illustrated) of the comparative example and the wave washers 23 used in the flexible member 1 of the Example 1 at the time of being bent at 90 degrees are compared to each other.

The flexible member of the comparative example has a main body part in which the wave washers 23A are stacked and joined to each other in a manner similar to that in the Example 1 and has the same constitution as the Example 1 except for the shapes of inner circumferences 23Ae of the wave washers 23A.

That is, in the comparative example, the inner circumferences 23Ae of the wave washers 23A have circular shapes and do not have the easily deformable parts 29 as in the Example 1.

In the wave washers 23A of the comparative example, deformation between the joint parts 21 is small, deformation in the vicinity of the joint parts 21 is significant, and there is a difference between the deformation amounts in the inner and outer circumferences 23Ae and 23Af.

As a result, in the comparative example, it can be seen that portions of a high stress are locally present on the inner circumference 23Ae side in regions along the joint parts 21A. The largest stress at this time was 1,186 MPa. FIG. 12 illustrates that the darker the color, the higher the stress (the same applies to FIG. 13).

In contrast, in the wave washers 23 of the Example 1, the easily deformable parts 29 are actively deformed between the joint parts 21 adjacent to each other in the circumferential direction. For this reason, the deformation amounts in the vicinity of the joint parts 21 can be reduced.

As a result, in the Example 1, regions in which a stress acts further spread in the circumferential direction toward a central part side between the joint parts 21 than those in the comparative example, and it can be seen that a stress acting on the regions along the joint parts 21 can be reduced. The largest stress at this time was 911 MPa.

[Effects of Example 1]

As described above, the flexible member 1 of the present example includes the main body part 19 that has a plurality of wave washers 23 stacked in the axial direction and joined to each other by a plurality of joint parts 21 and is able to be bent with respect to the axial direction due to elastic deformation of the wave washers 23, and the easily deformable parts 29 that are formed between the joint parts 21 adjacent to each other in the circumferential direction in each of the wave washers 23.

Therefore, in the present example, the linearity of load characteristics of a bending angle and a load can be enhanced, and it is possible to obtain a flexible member having excellent load resistance and flexibility while achieving reduction in size.

Furthermore, in the present example, the easily deformable parts 29 are actively deformed between the joint parts 21 in each of the wave washers 23 when the main body part 19 is bent. Accordingly, in the present example, a stress can be alleviated by reducing deformation in the vicinity of the joint parts 21 in each of the wave washers 23, and thus durability of the flexible member 1 can be improved.

In addition, the easily deformable parts 29 include: portions of the wave washer 23 having a relatively small dimension in the radial direction. Therefore, the easily deformable parts 29 can be easily and reliably realized by setting flat surface shapes of the wave washers 23.

Particularly, in the present example, since the easily deformable parts 29 are set by the recessed parts 29a in the radial direction provided in the inner circumference 23e of the wave washer 23, the easily deformable parts 29 can be easily and reliably realized by setting the inner circumference 23e.

Each of the plurality of joint parts 21 includes: welded parts 25 in linear shape, being extended from the inner circumference 23e side to the outer circumference 23f side of the wave washer 23.

For this reason, in the present example, the shapes of the joint parts 21 can be simplified, and thus the flexible member 1 can be easily manufactured.

In addition, in the present example, bending operation can be reliably performed due to expansion and contraction of the mountain parts 23a and the valley parts 23b of the main body part 19.

Moreover, in the present example, since the mountain parts 23a and the valley parts 23b abutting each other are joined to each other, it is possible to obtain the flexible member 1 having an excellent torsional rigidity.

In addition, in the present example, the plurality of wave washers 23 has the insertion holes 23d through which the driving wires 11 are inserted. Therefore, the main body part 19 can be utilized as a guide for the driving wires 11 so that the driving wires 11 can be retained at appropriate positions, and thus more stable and accurate bending operation can be performed.

Example 2

Figure 14:
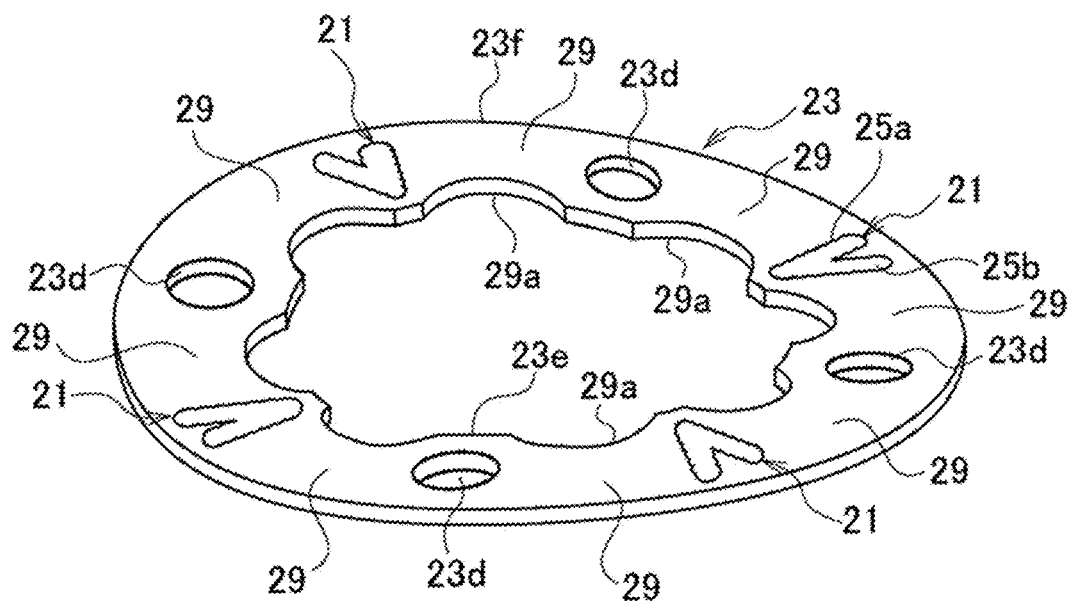
FIG. 14 is a perspective view illustrating a wave washer according to an Example 2 of the present invention.
Figure 15:
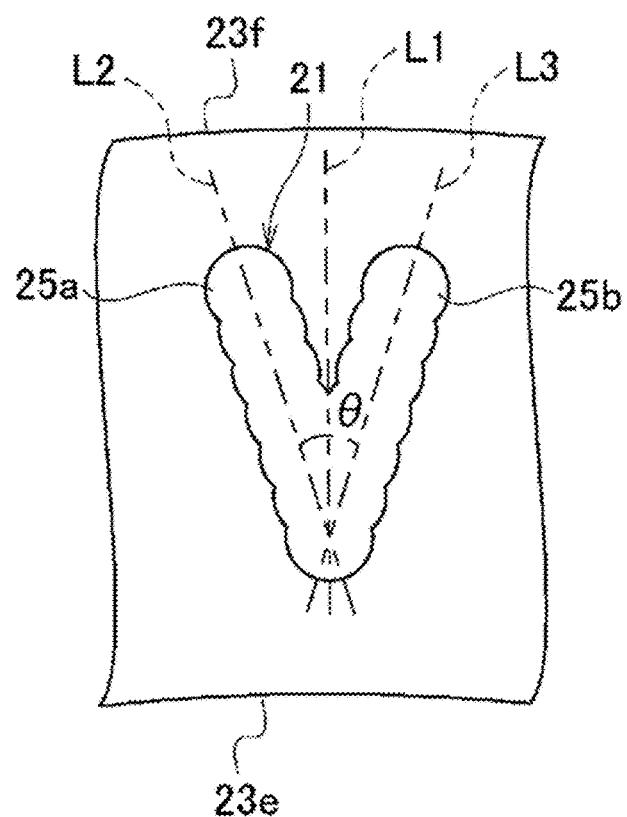
FIG. 15 is an enlarged plan view illustrating a main part in FIG. 14.

FIG. 14 is a perspective view illustrating a wave washer according to an Example 2 of the present invention. FIG. 15 is an enlarged plan view illustrating a main part in FIG. 14. In the Example 2, constitutions corresponding to those in the Example 1 are indicated by the same reference signs, and duplicate description will be omitted.

In the present example, the shapes of the joint parts 21 are changed compared to the Example 1. The constitutions are otherwise the same as those in the Example 1.

Each of the joint parts 21 of the present example includes: a pair of welded parts 25a and 25b in linear shape. The pair of welded parts 25a and 25b gradually separates from each other in the circumferential direction from the inner circumference 23e side toward the outer circumference 23f side of the wave washer 23. Accordingly, the joint parts 21 curb occurrence of a difference between the deformation amounts in the inner circumference 23e and the outer circumference 23f of the wave washer 23 when the main body part 19 of the flexible member 1 is bent.

In the present example, the pair of welded parts 25a and 25b is individually formed to have continuously linear shapes and forms a V-shape in which they overlap each other on the inner circumference 23e side of the wave washer 23.

In the pair of welded parts 25a and 25b, the welded part 25a on one side is formed on a second line L2, and the welded part 25b on the other side is formed on a third line L3. The second line L2 extends in a direction intersecting the first line L1 extending in the radial direction (radiating direction) from the center of the wave washer 23. The third line L3 extends in a direction intersecting the second line L2.

In the present example, the second line L2 and the third line L3 are disposed symmetrically with respect to the first line L1. An angle θ between the second line L2 and the third line L3 is within a range of 15 degrees to 30 degrees. Each of the welded parts 25a and 25b is formed to have a linear shape such that the centers of the welding spots 27 are positioned on the second line L2 and the third line L3. The opening angle between the welded parts 25a and 25b is within a range of 15 degrees to 30 degrees, particularly 20 degrees which coincide with the angle θ formed by the second line L2 and the third line L3.

According to the constitution, in the present example, when the flexible member 1 is bent, occurrence of a difference between the deformation amounts in the inner and outer circumferences 23e and 23f of each of the wave washers 23 in the flexible member 1 is curbed by the joint parts 21.

Specifically, as described above, the pair of welded parts 25a and 25b of the joint part 21 gradually separates from each other in the circumferential direction from the inner circumference 23e side toward the outer circumference 23f side. For this reason, in the outer circumference 23f of the wave washer 23, deformation in portions corresponding to portions between the welded parts 25a and 25b is curbed.

On the other hand, in the inner circumference 23e of the wave washer 23, since the welded parts 25a and 25b approach each other and they overlap each other in the present example, there is no curbing of deformation as in the outer circumference 23f.

Therefore, in each of the wave washers 23, the deformation amounts in the inner and outer circumferences 23e and 23f are adjusted, and occurrence of a difference between the deformation amounts in the inner and outer circumferences 23e and 23f of the wave washer 23 is curbed.

Accordingly, in the present example, deviation in stress acting on portions around the joint parts 21 is curbed, and thus durability of the flexible member 1 is improved.

The shapes of the welded parts 25a and 25b can be suitably formed in accordance with the difference between the deformation amounts in the inner and outer circumferences 23e and 23f of the wave washer 23. For example, the shapes of the welded parts 25a and 25b are not limited to linear shapes and may be curves or the like. In addition, the opening angle and the lengths of the welded parts 25a and 25b can also be changed in accordance with the difference between the deformation amounts in the inner and outer circumferences 23e and 23f of the wave washer 23.

In addition, the joint parts 21 of the present example are at intervals from the inner circumference 23e and the outer circumference 23f of the wave washer 23 in a plan view, but they can have shapes lying from the inner circumference 23e to the outer circumference 23f.

Moreover, the welded parts 25a and 25b may have shapes not overlapping on the inner circumference 23e side.

In addition, the shape of only one of the welded parts 25a and 25b may be changed.

Figure 16:
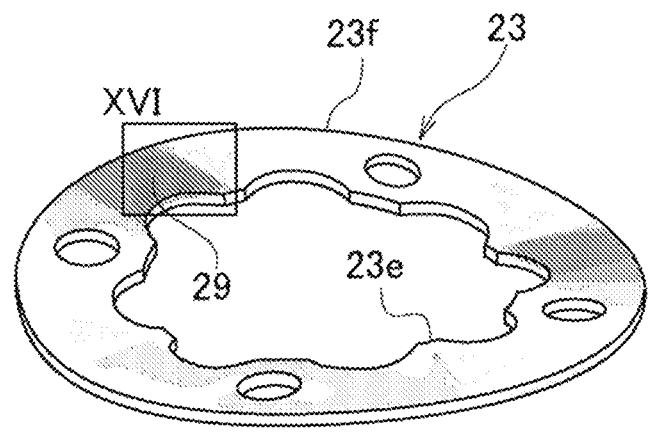
In FIG. 16, (A) and (B) illustrate a stress distribution of the wave washer in FIG. 14, in which (A) of FIG. 16 illustrates a perspective view of the wave washer in its entirety, and (B) of FIG. 16 is an enlarged view of the XVI part in (A) of FIG. 16.
Figure 16:
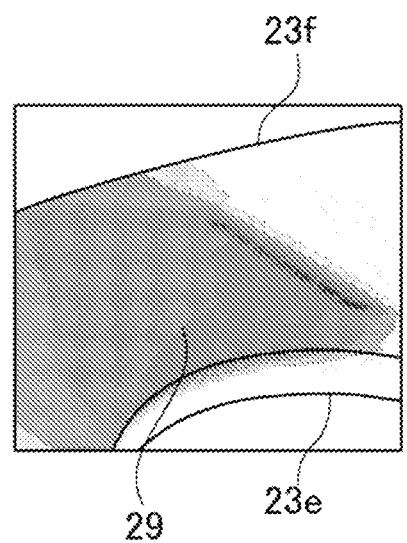
Figure 17:
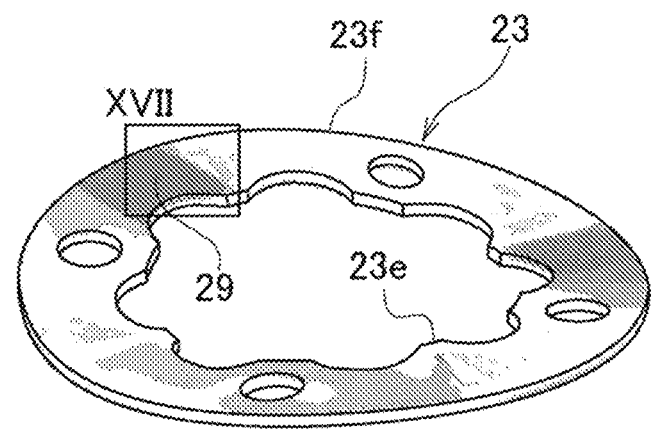
In FIG. 17, (A) and (B) illustrate a stress distribution of the wave washer in FIG. 14, in which (A) of FIG. 17 illustrates a perspective view of the wave washer in its entirety, and (B) of FIG. 17 is an enlarged view of the XVII part in (A) of FIG. 17.
Figure 17:
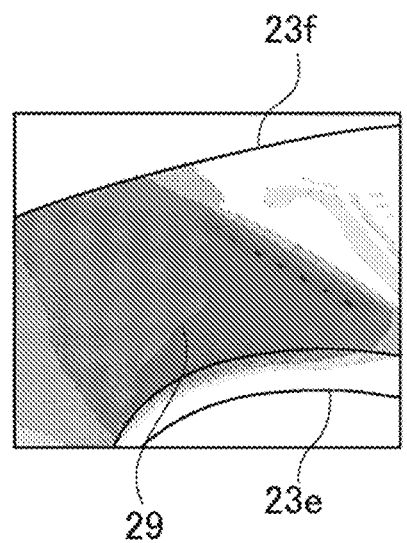
Figure 18:
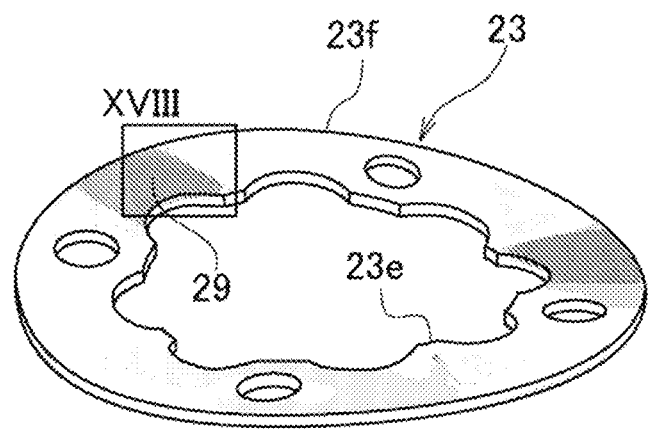
In FIG. 18, (A) and (B) illustrate a stress distribution of the wave washer in FIG. 14, in which (A) of FIG. 18 illustrates a perspective view of the wave washer in its entirety, and (B) of FIG. 18 is an enlarged view of the XVIII part in (A) of FIG. 18.
Figure 18:
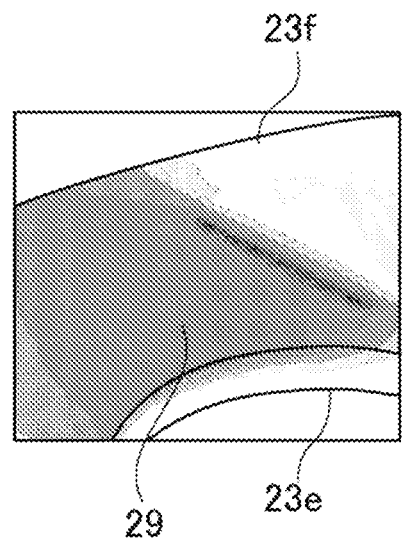
Figure 19:
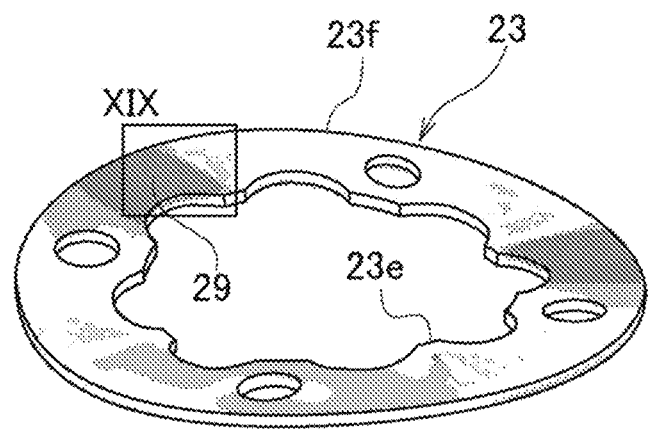
In FIG. 19, (A) and (B) illustrate a stress distribution of the wave washer in FIG. 14, in which (A) of FIG. 19 illustrates a perspective view of the wave washer in its entirety, and (B) of FIG. 19 is an enlarged view of the XIX part in (A) of FIG. 19.
Figure 19:
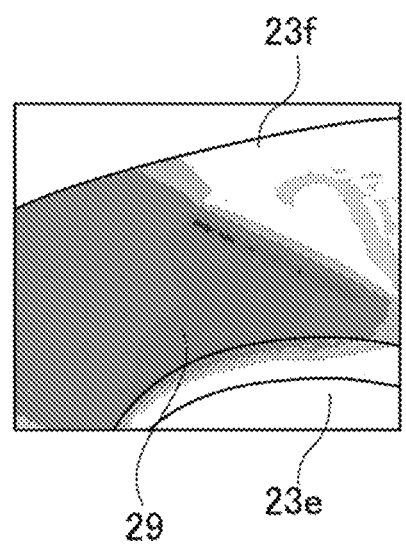
Figure 20:
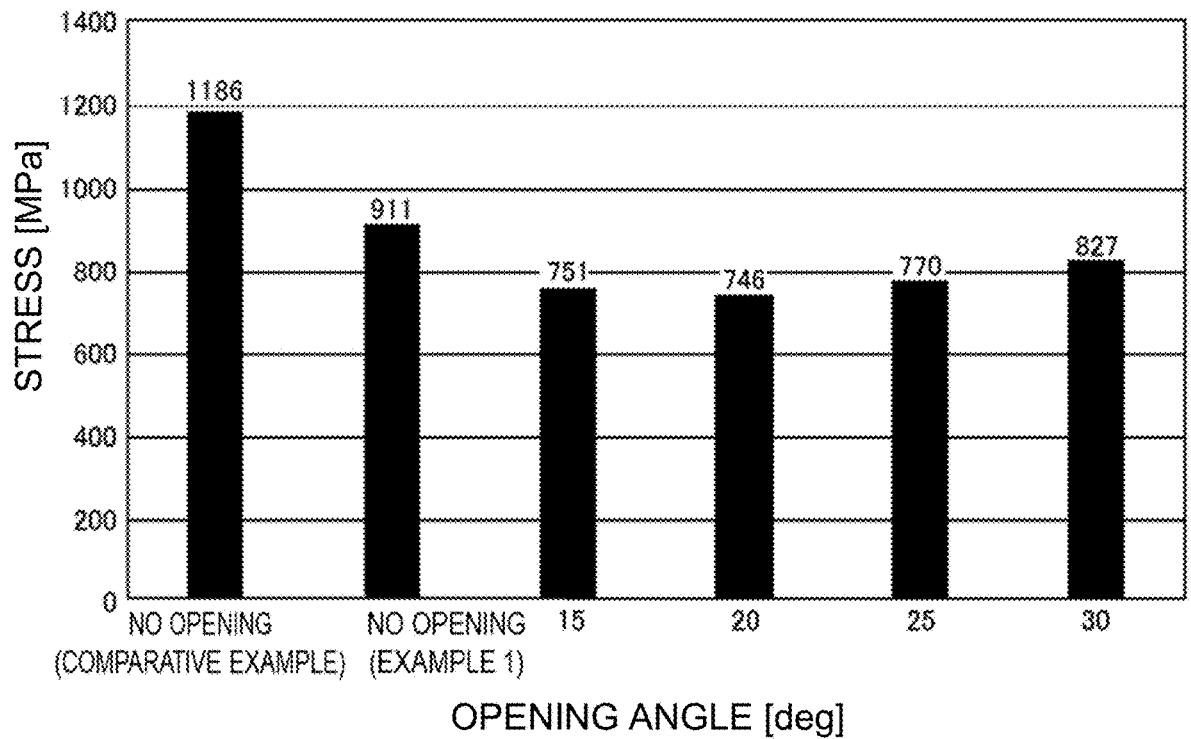
FIG. 20 is a graph illustrating a largest stress in the Example 2 together with largest stresses in the comparative example in FIG. 12 and the Example 1 in FIG. 13.

Similar to FIG. 13, FIG. 16 to FIG. 19 illustrate stress distributions of the wave washer 23 according to the Example 2. FIG. 16 illustrates that the opening angle between the welded parts 25a and 25b of the joint part 21 is 15 degrees, FIG. 17 illustrates that it is 20 degrees, FIG. 18 illustrates that it is 25 degrees, and FIG. 19 illustrates that it is 30 degrees, respectively. FIG. 20 is a graph illustrating the largest stress in the Example 2 in FIG. 16 to FIG. 19 together with the largest stresses in the comparative example in FIG. 12 and the Example 1 in FIG. 13.

As described in the foregoing Example 1, in the flexible member of the comparative example in FIG. 12, a difference occurs between the deformation amounts in the inner and outer circumferences 23Ae and 23Af at the time of being bent, portions of a high stress (1,186 MPa at the maximum) are locally present in regions along the joint parts 21A.

In contrast, in the Example 1, as described in the foregoing Example 1, a stress acting on regions along the joint parts 21 can be reduced to 911 MPa at the maximum.

Moreover, in the present example, since the difference between the deformation amounts in the inner and outer circumferences 23e and 23f at the time of being bent is curbed, a stress is made uniform from the inner circumference 23e side to the outer circumference 23f side in regions along the joint parts 21.

As a result, in the present example, when the opening angle between the welded parts 25a and 25b is 15 degrees, 20 degrees, 25 degrees, and 30 degrees, the largest stress is reduced to 751 MPa, 746 MPa, 770 MPa, and 827 MPa, respectively.

Therefore, in the present example, it can be seen that the opening angle between the welded parts 25a and 25b is preferably set within a range of 15 degrees to 30 degrees, particularly 20 degrees.

As described above, in the flexible member 1 of the present example, each of the plurality of joint parts 21 includes: the pair of welded parts 25a and 25b in linear shape which gradually separates from each other in the circumferential direction from the inner circumference 23e toward the outer circumference 23f of the wave washer 23.

Therefore, in the present example, occurrence of a difference between the deformation amounts in the inner and outer circumferences 23e and 23f when the wave washers 23 are deformed due to the pair of welded parts 25a and 25b is curbed. Therefore, in the present example, deviation in stress acting on portions around the joint parts 21 in each of the wave washers 23 can be curbed. As a result, in the present example, the largest stress acting on portions around the joint parts 21 can be more reliably reduced, and thus durability of the flexible member 1 can be improved.

In the pair of welded parts 25a and 25b, the welded part 25a on one side is formed on the second line L2 extending in a direction intersecting the first line L1 extending in the radial direction from the center of the wave washer 23, and the welded part 25b on the other side is formed on the third line L3 extending in a direction intersecting the second line L2.

For this reason, in the present example, at least one of the welded parts 25a and 25b can reliably intersect the first line L1, and thus deviation in stress acting on portions around the joint parts 21 in each of the wave washers 23 can be reliably curbed.

In addition, each of the pair of welded parts 25a and 25b is formed to have a continuously linear shape. Therefore, a stress can be made uniform along the welded parts 25a and 25b.

In addition, the pair of welded parts 25a and 25b has a V-shape in which they overlap each other on the inner circumference 23e side of the wave washer 23. Therefore, the deformation amount in the inner circumference 23e of the wave washer 23 is not carelessly curbed. For this reason, the pair of welded parts 25a and 25b can reduce adjustment of the deformation amount in the outer circumference 23f of the wave washer 23.

The opening angle between the pair of welded parts 25a and 25b is 20 degrees. Therefore, deviation in stress can be more reliably curbed, and thus the largest stress can be more reliably reduced.

Furthermore, in the present example as well, it is possible to exhibit operational effects similar to those in the Example 1.

Example 3

Figure 21:
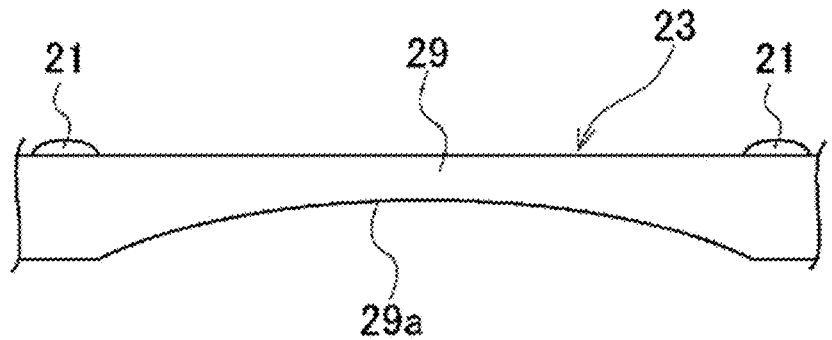
FIG. 21 is a side view schematically illustrating an easily deformable part of a wave washer according to an Example 3 of the present invention.

FIG. 21 is a side view schematically illustrating an easily deformable part of a wave washer according to an Example 3 of the present invention. In the Example 3, constitutions corresponding to those in the Example 1 are indicated by the same reference signs, and duplicate description will be omitted.

In the present example, the easily deformable parts 29 include: portions of the wave washer 23 having a relatively small plate thickness. The constitutions are otherwise the same as those in the Example 1, but they may be the same constitutions as those in the Example 2.

Regarding the easily deformable parts 29, the plate thickness of the wave washer 23 gradually decreases as it is separated from the joint part 21 side. Accordingly, lower surfaces 29b of the easily deformable parts 29 have arc shapes. If the plate thicknesses of the easily deformable parts 29 are smaller than those of the joint parts 21, the shapes may not be limited to arc shapes. For example, recessed shapes or the like are also conceivable.

According to the Example 3 as well, it is possible to exhibit operational effects similar to those in the Example 1.

The invention claimed is:

1. A flexible member comprising:
a main body part that has a plurality of wave washers stacked in an axial direction and joined to each other by a plurality of joint parts, and the main body part is able to be bent with respect to the axial direction due to elastic deformation of the wave washers; and
easily deformable parts that are formed between the joint parts adjacent to each other in a circumferential direction in each of the wave washers, and the easily deformable parts are more readily deformable than other portions in the wave washers;
wherein each of the plurality of joint parts includes: welded parts in linear shape, being extended from an inner circumferential side toward an outer circumferential side of each of the plurality of wave washers;
wherein each of the joint parts includes a pair of the welded parts, and
wherein the pair of the welded parts gradually separates from each other in the circumferential direction from the inner circumferential side toward the outer circumferential side in each of the plurality of wave washers;
wherein the pair of the welded parts has a V-shape in which the welded parts overlap each other on the inner circumferential side in each of the plurality of wave washers;
wherein an opening angle between the pair of the welded parts is within a range of 15 degrees to 30 degrees.

2. The flexible member according to claim 1,
wherein the easily deformable parts include: portions of each of the plurality of wave washers having a relatively small dimension in a radial direction of each of the plurality of wave washers.

3. The flexible member according to claim 2,
wherein the easily deformable parts are divided by recessed parts formed in the radial direction in an inner circumference of each of the plurality of wave washers.

4. The flexible member according to claim 1,
wherein the easily deformable parts include: portions of each of the plurality of wave washers having a relatively small plate thickness smaller than that of each of the plurality of joint parts.

5. The flexible member according to claim 1,
wherein each of the plurality of wave washers includes a plurality of mountain parts and valley parts between the mountain parts in the circumferential direction, mountain parts and valley parts of adjacent wave washers abut each other, and abutment portions of the mountain parts and the valley parts are joined to each other by the joint parts.

* * * * *